US012337083B2

(12) United States Patent
Lan et al.

(10) Patent No.: US 12,337,083 B2
(45) Date of Patent: Jun. 24, 2025

(54) GERMICIDAL DEVICE

(71) Applicant: SHENZHEN GUANKE TECHNOLOGIES CO., LTD, Shenzhen (CN)

(72) Inventors: Qing Lan, Shenzhen (CN); Shoubao Chen, Shenzhen (CN); Ligen Liu, Shenzhen (CN)

(73) Assignee: SHENZHEN GUANKE TECHNOLOGIES CO., LTD, Shenzhen (CN)

( * ) Notice: Subject to any disclaimer, the term of this patent is extended or adjusted under 35 U.S.C. 154(b) by 64 days.

(21) Appl. No.: 17/434,134

(22) PCT Filed: May 13, 2021

(86) PCT No.: PCT/CN2021/093692
§ 371 (c)(1),
(2) Date: Nov. 17, 2022

(87) PCT Pub. No.: WO2022/236786
PCT Pub. Date: Nov. 17, 2022

(65) Prior Publication Data
US 2024/0016967 A1   Jan. 18, 2024

(51) Int. Cl.
*A61L 9/20* (2006.01)
(52) U.S. Cl.
CPC ............ *A61L 9/20* (2013.01); *A61L 2209/12* (2013.01)

(58) Field of Classification Search
None
See application file for complete search history.

(56) References Cited

U.S. PATENT DOCUMENTS

| 10,808,964 | B2 * | 10/2020 | Polidoro | F21S 8/033 |
| 2017/0056543 | A1 * | 3/2017 | Mole | A61L 9/22 |
| 2017/0321877 | A1 * | 11/2017 | Polidoro | F24F 13/28 |
| 2018/0133355 | A1 * | 5/2018 | Kirschman | A61L 9/18 |
| 2021/0187151 | A1 * | 6/2021 | Kirschman | A61L 2/08 |

FOREIGN PATENT DOCUMENTS

| CN | 111701066 A | * | 9/2020 | | A61L 9/20 |
| CN | 212617982 U | * | 2/2021 | | |
| KR | 102087802 B1 | * | 3/2020 | | |

* cited by examiner

*Primary Examiner* — Andrew Smyth
(74) *Attorney, Agent, or Firm* — Maier & Maier, PLLC

(57) ABSTRACT

A germicidal device that includes a lamp cap, a grating component, a lamp body, a germicidal component and a fan component, where the grating component is provided with a central hole and several baffles which are provided at intervals to form several light outlets; the germicidal component is provided in the central hole for emitting UV light part of which is emitted via the light outlets; the bottom of the lamp body is provided with the first ventilation hole which connects to the central hole; the fan component is provided corresponding to the first ventilation hole for ventilation of the germicidal device.

10 Claims, 7 Drawing Sheets

GERMICIDAL DEVICE

FIELD

The present invention relates to the technical field of lighting and sterilization equipment, particularly to a germicidal device.

BackgroundLarge and medium-power UV disinfection lights usually refer to lights whose power is higher than 20 W. Strong UV light emitted by such lights can achieve an excellent sterilization and disinfection effect and shorten the sterilization time. Strong-UV lights mainly adopt three sterilization and disinfection modes: direct illumination, ventilation and horizontal illumination. Their service characteristics are as shown below:

(1) Direct illumination UV lights: Such lights directly expose UV light to an open environment for sterilization and disinfection of object surfaces and air, achieving a high sterilization and disinfection effect; however, people should not stay in the sterilization environment when such lights are working, so their safety performance is poor.

(2) Ventilation UV lights: Such lights inhale air into the enclosed light cavity, after UV sterilization and disinfection in the light cavity, sterilized air is exhausted out of the light to finish air sterilization and disinfection and ventilation. They are mainly used for air disinfection. People do not need to leave the sterilization place when such lights are working, so people can be protected from the damage of UV light and the safety performance is high; however, the sterilization efficiency is low, noises are likely to occur during ventilation, and products are usually designed into large-size cabinets, so they have a large volume and heavy weight.

(3) Horizontal illumination UV lights: UV lights are installed at the height above 2.1 m (i.e. the upper space) to carry out sterilization and disinfection of the upper space. People can carry out activities in the space below 2.1 m, the safety performance of such lights is high, and people do not need to leave the sterilization environment when such lights are working. In relevant technologies, horizontal illumination UV lights have a very poor air sterilization effect for the lower space, and products are usually designed into large-size cabinets, so they have a large volume and heavy weight.

To improve the use safety of the UV germicidal light and overcome the defect of low sterilization efficiency of ventilation and horizontal illumination UV lights, the air ventilation efficiency of ventilation UV lights needs to be improved, that is, the light cavity needs to be increased, and the fan power needs to be improved, while horizontal UV lights need large-power UV light sources and require further emission distance of UV light. As a result, ventilation UV lights and horizontal UV lights are featured with a complex structure, a big volume and heavy weight as well as difficulty in product installation and a high cost.

The foregoing content is only used for assisting in understanding the technical scheme of this invention, but does not mean the acknowledgement of that the above content is the current technology.

SUMMARY

The main objective of the present invention is to provide a germicidal device to solve technical problems of existing strong-UV lights, such as low sterilization efficiency, complex structure, big volume, heavy weight, installation difficulty and high cost.

To realize the above objective, the germicidal device in this present invention comprises a lamp cap, a grating component, a lamp body, a germicidal component and a fan component, wherein the lamp cap and the lamp body are provided at both ends of the grating component respectively; it is defined as that the arrangement direction of the lamp cap, the grating component and the lamp body is the first direction;

the grating component is provided with a central hole and several baffles, and several baffles are provided at intervals to form several light outlets; several the light outlets connect to the central hole, several the light outlets extend along the periphery of the grating component, and the light emission direction of several the light outlets is vertical to the first direction;

the germicidal component is provided in the central hole for emitting UV light part of which is emitted via the light outlets;

the bottom of the lamp body is provided with the first ventilation hole which connects to the central hole;

the fan component is provided corresponding to the first ventilation hole for ventilation of the germicidal device.

Other characteristics and corresponding beneficial effects of the present invention are elaborated in the latter part of the description.

The technical problem solving thinking of the invention is as follows: Taking the germicidal device—UV light as an example, the UV light source of the UV lights is designed into a circular structure (circular structure, oval structure, square structure or other circular structure), the grating component is provided on the outer side of the circular UV light source to limit that the UV light is only emitted horizontally. In the meanwhile, the bottom of the UV light is provided with a fan and a ventilation hole (preferentially, the fan blows air downward vertically), sterilized air in the upper space can be better exhausted by the fan, which promotes ventilation of air in the upper space and air in the lower space, expands the sterilization scope of peripheral air by the UV light, enables the UV light to directly sterilize and disinfect horizontal air corresponding to the grating component and enables better convection between horizontal air and vertical air to realize indirect sterilization and disinfection of air in other areas beyond the horizontal level corresponding to the grating component.

Compared with ordinary horizontal illumination UV lights, instead of adopting a larger-power UV light source to achieve further UV light emission distance and expand the sterilization scope, the new UV light solution is provided with a fan component at its bottom, which enables the horizontal illumination light in the upper space to directly sterilize and disinfect air in the lower space.

The grating component adopts the sheet stamping process, which can significantly reduce the weight of the grating component; there is a central hole in the center of the grating component, and the UV light source module (i.e. the germicidal component), the fan component and other parts are provided inside the central hole, significantly reducing the size of the light. The size of the new product of the present invention can be shrunk to φ250×200 MM, enabling a compact structure; ventilation UV lights and horizontal illumination UV lights are usually designed into cabinets.

Their maximum size will usually be more than 0.6 m or 1 m, and they are heavy, so it is hard that they are installed by an individual person.

In addition, the upper part of the grating component is provided with a lamp cap used for fixing UV lights. The lamp cap may be of a standard lamp cap structure, a fixing seat structure, a hook structure or an embedded installation structure to facilitate external installation of UV lights. In the present invention, the size of the light can be less than 250 mm, and its weight can be less than 1.7 Kg. When the lamp cap is of a standard screw base, the lamp can serve as the electric light source and can be directly installed into traditional lights or onto traditional lamp seats for use. The electric light source can meet the requirement for safety certification of lights and has a new application prospect.

The shape, dimension, proportion or position relationship of parts of the product in drawings may be real data of embodiments and they are under protection of this invention.

DETAILED DESCRIPTION OF THE EMBODIMENTS

To make the objective, technical solutions and advantages of the present invention clearer and be understood better, further detailed descriptions of examples of the present invention are made in combination with drawings. Understandably, the specific examples described are just used to explain but not limit the present invention.

The present invention provides a germicidal device 100 which can be a UV germicidal light used for sterilizing air.

Figure 1:
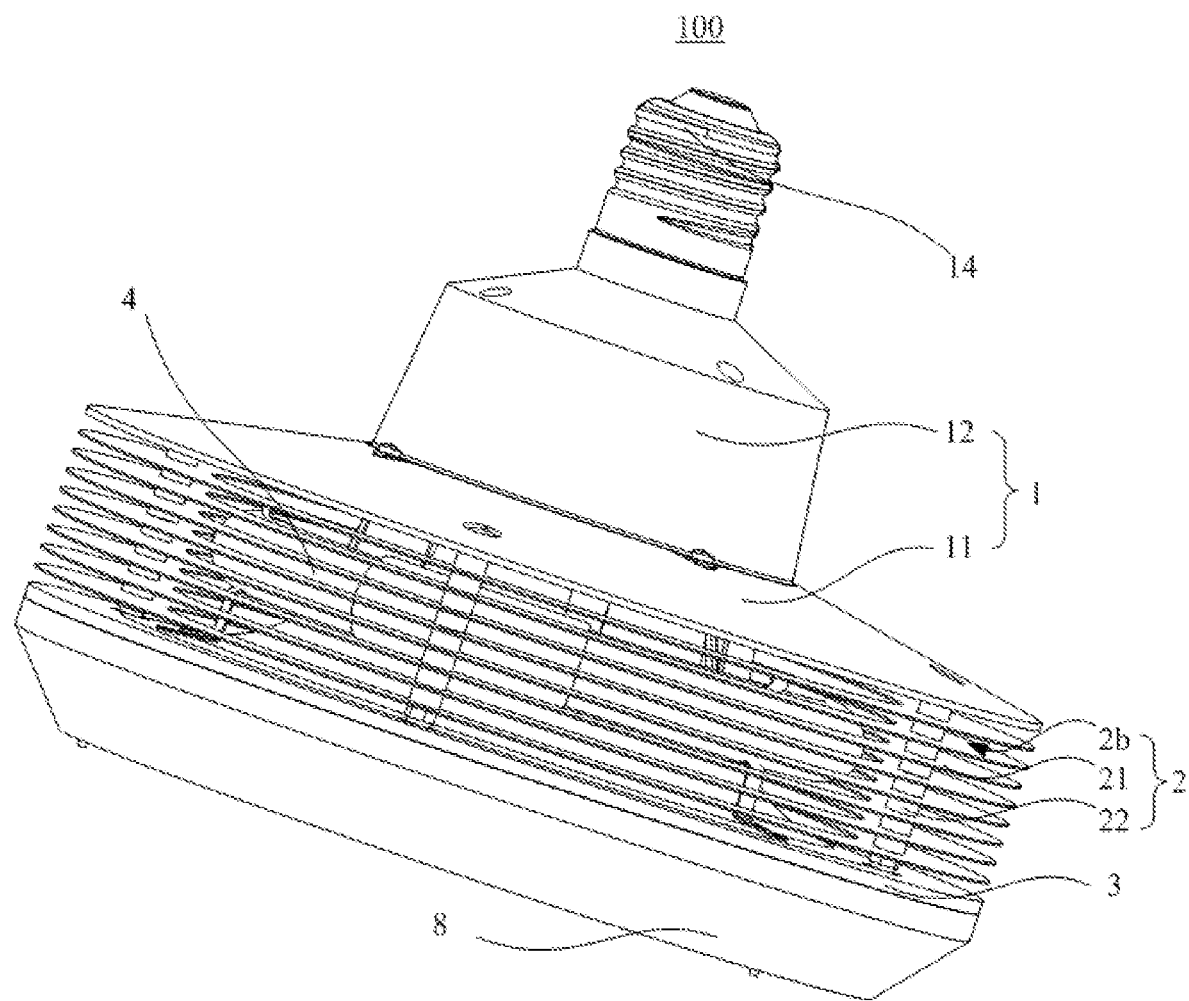
FIG. 1 is a schematic diagram showing the structure of an example of the germicidal device of the present invention.
Figure 2:
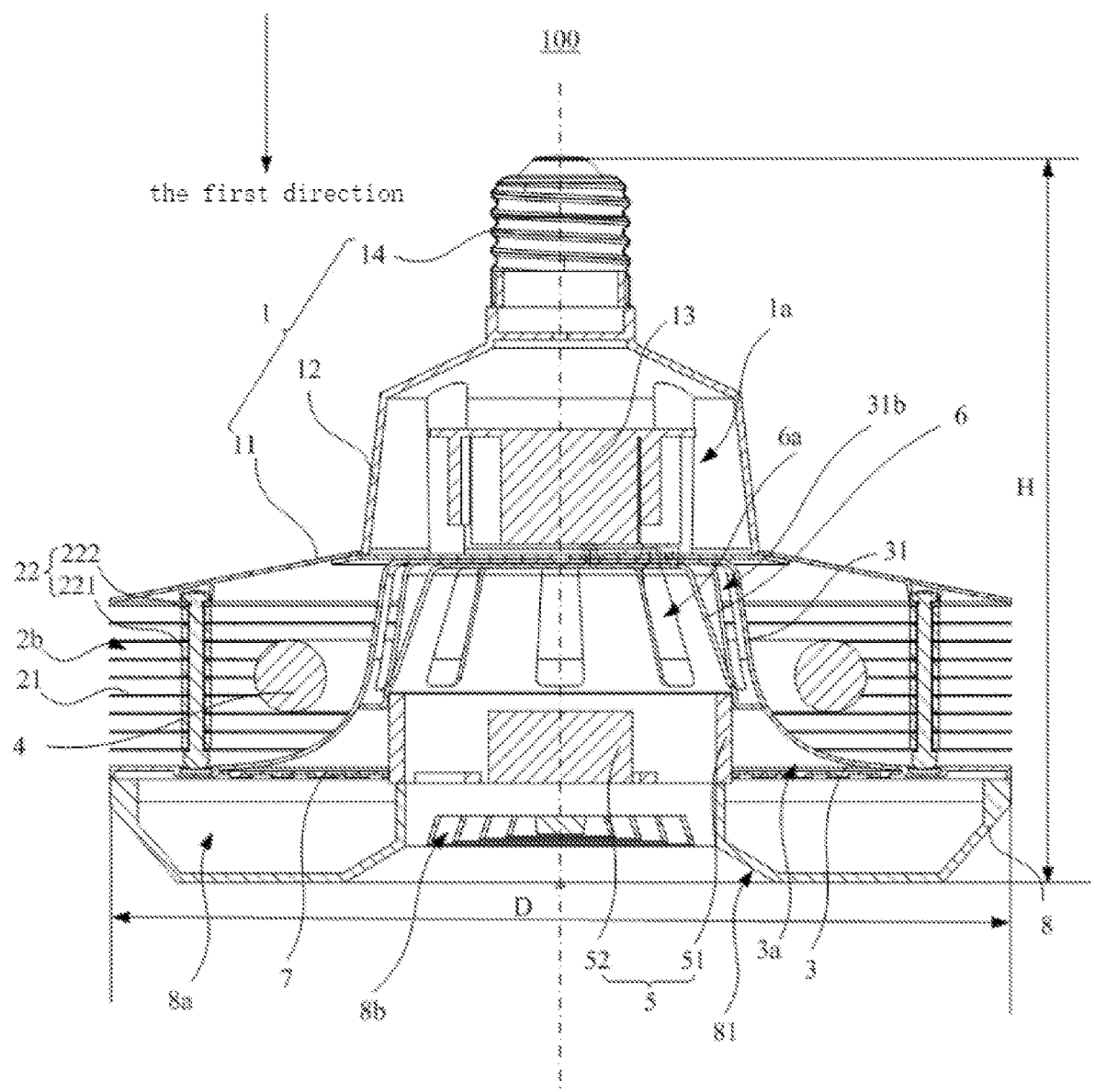
FIG. 2 is a schematic diagram of the cross section of the device in FIG. 1.
Figure 3:
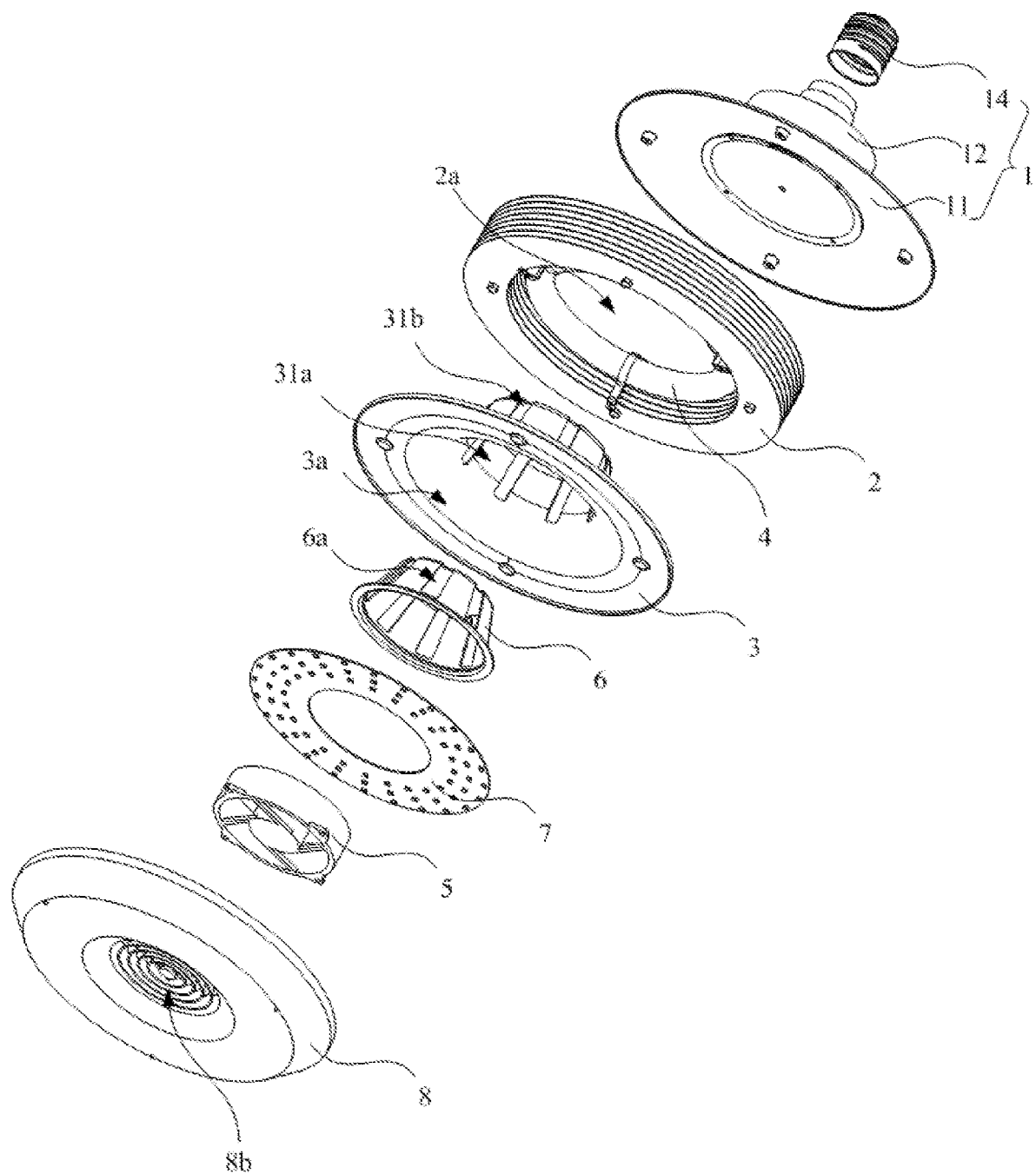
FIG. 3 is the breakdown diagram of the device in FIG. 1.

In one example of the present invention, as shown in FIGS. 1-3, the germicidal device 100 comprises a lamp cap 1, a grating component 2, a lamp body 3, a germicidal component 4 and a fan component 5, wherein the lamp cap 1 and the lamp body 3 are provided on both ends of the grating component 2; it is defined as that the arrangement direction of lamp cap 1, grating component 2 and lamp body 3 is the first direction;

the grating component 2 is provided with a central hole 2a and several baffles 21, several baffles 21 are provided at intervals to form several light outlets 2b; several light outlets 2b connect to the central hole 2a, several light outlets 2b extend along the periphery of the grating component 2, and the light illumination direction of several light outlets 2b is vertical to the first direction;

the germicidal component 4 is provided in the central hole 2a for emitting UV light part of which is emitted via the light outlets 2b;

the bottom of the lamp body 3 is provided with the first ventilation hole 3a which connects to the central hole 2a;

the fan component 5 is provided corresponding to the first ventilation hole 3a for ventilation of the germicidal device 100.

In this example, the first direction can be the gravity direction, i.e. the vertical direction. The germicidal device 100 can be installed in the upper space of the space to be sterilized via the lamp cap 1, and the installation height is usually more than 2.1 m from the ground, so that air in the upper space is directly sterilized. The light outlets 2b are provided along the periphery of the grating component 2, and light is emitted via the light outlets 2b horizontally. The germicidal device 100 realize sterilization with the UV light emitted by the germicidal component 4.

In this example, the lamp cap 1 provided on the top of the grating component 2 is used for fixing the germicidal device 100 to external devices. And the standard screw base structure, the fixing seat structure or the hook structure can be adopted to facilitate external installation. In the present invention, as shown in FIG. 2, the outline diameter of the germicidal device can be less than 250 mm, and its weight can be less than 1.7 Kg. When the lamp cap is of a standard screw base, the germicidal device can serve as the electric light source and can be directly installed into traditional lights or onto traditional lamp seats for use. The electric light source can meet the requirement for safety certification of lights and has a new application prospect.

In this example, the germicidal component 4 is provided inside the central hole 2a. The germicidal component 4 can be a circular UV lamp tube or can be composed of several UV light modules arranged along the periphery; The germicidal component 4 can also be composed of several circular UV lamp tubes stacked up vertically to increase the power of the UV sterilization module.

In this example, the germicidal component 4 is a circular lamp tube, grating component 2 is circular, so that installation of the germicidal device 100 is not restricted in four directions, installation is more flexible, and the UV sterilization scope is improved. In addition, the circular lamp tube is an independent light source which makes the overall structure more compact.

The germicidal component 4 can be a UV lamp tube which comprises a UV light source and the corresponding driving power supply. The UV light source may be one or several kind/s of gas discharge UV lamp tube light sources like UV LED lamp bead component, low-pressure mercury lamp (LPM), high and medium-pressure mercury lamp, xenon lamp, etc.

The fan component 5 can enhance the wind power for exhausting air and improve the wind speed of exhausting air to exhaust air faster and further, promote ventilation and circulation of air sterilized and to be sterilized outside the germicidal device 100 and improve the air sterilization efficiency. In the meanwhile, partial UV light emitted by germicidal component 4 can be emitted via the light outlets 2b to directly sterilize and disinfect external air; since the germicidal component 4 and the light outlets 2b are provided along the periphery, the effective area of direct sterilization and disinfection with UV light can be increased.

In this embodiment, the germicidal device serves as the UV light, the germicidal component 4 is a UV lamp tube, the UV lamp tube can emit UV light source, the germicidal component 4 is designed into a circular structure (circular structure, oval structure, square structure or other circular structure applicable), the outer side of the circular UV light source is provided with a grating component 2 to limit that the UV light is only emitted horizontally. In the meanwhile, the bottom of the germicidal component 4 is provided with a fan component 5 and a first ventilation hole 2a, optionally, the fan component 5 blows air downward vertically, sterilized air in the upper space can be better exhausted by the fan component 5, which promotes ventilation of air in the upper space and air in the lower space, expands the sterilization scope of peripheral air by the germicidal component 4, enables the UV light to directly sterilize and disinfect horizontal air corresponding to the grating component 2 and enables better convection between horizontal air and vertical air to realize indirect sterilization and disinfection of air in other areas beyond the horizontal level corresponding to the grating component.

Understandably, the fan component 5 is provided corresponding to the first ventilation hole 3a, which shortens the air flue distance composed of the light outlets 2b, the central hole 2a and the first ventilation hole 3a, facilitating the ventilation efficiency. The fan component 5 adopts the following ventilation mode: the fan component 5 blows air along the first direction, the light outlets 2b are air inlets, and the first ventilation hole 3a is the air outlet. Or, the fan component adopts the following ventilation mode: the fan component blows air in the direction opposite to the first direction, the light outlets 2b are the outlets, and the first ventilation hole 3a is the air inlet.

In this example, baffles 21 are provided at intervals to form light outlets 2b, which limits that the UV light is only emitted via the light outlets 2b. the light outlets 2b extend along the periphery of the grating component 2, which can improve the UV sterilization scope and sterilization efficiency. In one example, the inner wall of the light outlets 2b light outlets 2b is provided with a light absorption layer, one side of the baffles 21 facing the light outlets 2b is provided with a light absorption layer to reduce reflection of UV light on the baffles 21 and prevent UV light from being emitted via light outlets 2b in a scattered way after times of reflection.

Figure 5:
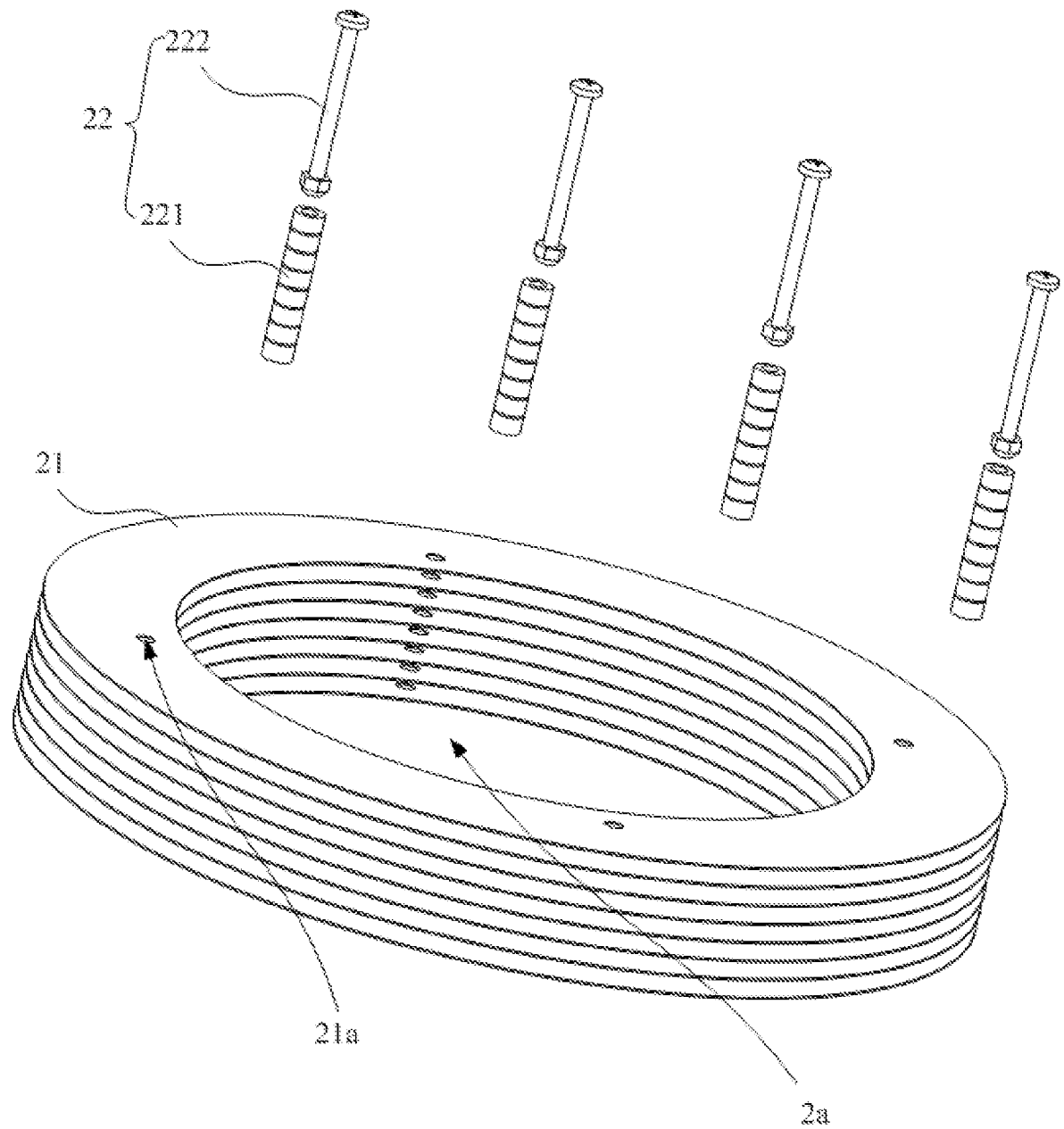
FIG. 5 is the breakdown diagram of the grating component in FIG. 3.

As shown in FIG. 1, FIG. 2 and FIG. 5, several the baffles 21 are provided in the first direction at intervals and in parallel, adjacent two the baffles 21 form a the light outlet 2b; the middle of each the baffle 21 is provided with the first through-hole, several the first through-holes are connected to form the central hole 2a in an enclosing way.

The baffles 21 adopt the sheet stamping process, which can significantly reduce the weight of the grating component; there is a central hole in the center of the grating component, and the germicidal component, the fan component and other parts are provided inside the central hole, significantly reducing the size of the light. As shown in FIG. 2, the outline diameter (D) of the present invention can be as small as 250 mm, and its height can be as small as 200 mm, enabling a compact structure.

As shown in FIG. 5, the grating component 2 is also provided with several connecting poles 22, the periphery of connecting poles 22 are provided with several locating grooves, several locating grooves are provided at intervals, several baffles 21 are arranged along the first direction, each baffle 21 is provided with a positioning hole 21a, each connecting pole 22 passes through several positioning holes 21a, and the part of the baffle 21 nearby the positioning hole 21a is accommodated in the locating groove. Understandably, locating of several baffles 21 can be realized via connecting poles 22.

As shown in FIG. 5, the connecting poles 22 comprise a locating piece 221 and a locking piece 222, the periphery of the locating piece 221 is provided with several locating grooves, each locating piece 221 passes through several positioning hole 21a, locating of several baffles 21 can be realized via the locating piece 221. In the meanwhile, the locating piece 221 is provided with a locking cavity in the first direction, the locking piece 222 passes through the locking cavity, both ends of the locking piece 222 are against the lamp body 3 and the lamp cap 1 respectively to limit the location relationship of the lamp cap 1, grating component 2 and lamp body 3 to realize dismountable connection of the lamp cap 1 and the grating component 2 and facilitate replacement of the germicidal component 4.

In one example of the present invention, as shown in FIG. 2, the germicidal device 100 also comprises a protruding part 31 provided in the central hole 2a, corresponding to the first ventilation hole 3a and connecting to the lamp cap 1 and the lamp body 3; the germicidal component 4 is provided around the protruding part 31.

The protruding part 31 is provided with the second ventilation hole 31b, and the first ventilation hole 3a and the central hole 2a connect to the second ventilation hole respectively.

Understandably, UV light emitted by the germicidal component is reflected on the protruding part 31, making more UV light be reflected via the light outlets 2b. In the meanwhile, the protruding part 31 can also be used for fixing the germicidal component 4 and/or the fan component 5.

In this example, the periphery or the top of the protruding part 31 is provided with the second ventilation hole 31b, the first ventilation hole 3a and the central hole 2a connect to the second ventilation hole 31b respectively to guarantee smooth ventilation of the germicidal device.

As shown in FIG. 2, in this example, the protruding part 31 and the lamp body 3 are designed into an integrated structure, and the protruding part 31 extends towards the lamp cap 1. In some other examples, both ends of the protruding part 31 connect to the lamp cap 1 and the lamp body 3 respectively in a dismountable way.

In another example of the present invention, the protruding part 31 can also connect to the lamp cap 1 or the grating component. The protruding part 31 and the lamp cap 1 are designed into an integrated structure or connect to each other in a dismountable way. Optionally, the protruding part 31 and the lamp cap 1 are designed into an integrated structure, and the protruding part 31 extends towards the lamp body 3.

In another example of the present invention, the protruding part 31 connects to the lamp body 3. The protruding part 31 and the lamp body 3 are designed into an integrated structure or connect to each other in a dismountable way.

Figure 4:
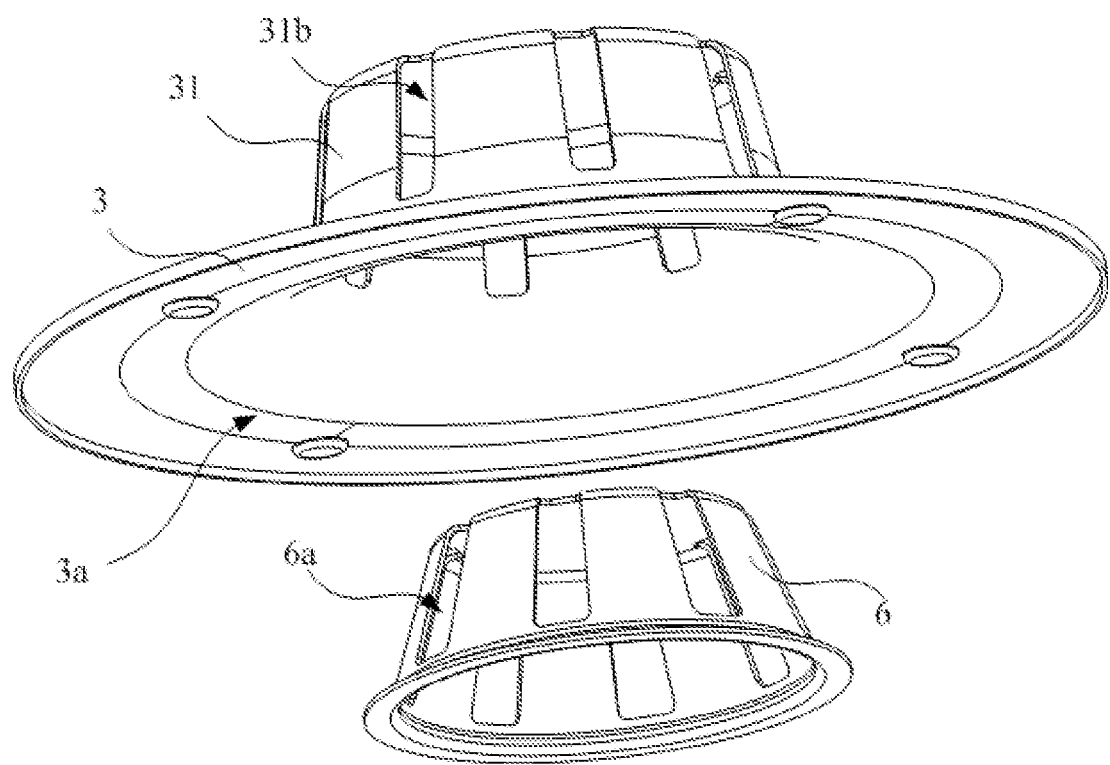
FIG. 4 is a schematic diagram of the lamp body and the light shield in FIG. 3.

In one example of the present invention, as shown in FIGS. 2-4, the protruding part is provided with the first accommodating cavity 31a, the first ventilation hole 3a and the second ventilation hole 31b second ventilation hole 31b connect to the first accommodating cavity 31a respectively; the germicidal device 100 also comprises a light shield 6 which is made of anti-UV material. The light shield 6 is provided inside the first accommodating cavity 31a and provided with the third ventilation hole 6a, the third ventilation hole 6a and the second ventilation hole 31b are provided at different positions, preventing the UV light from being emitted onto the fan component via the second ventilation hole 31b or onto the outside of the germicidal device via the first ventilation hole 3a.

Understandably, the light shield is provided with the third ventilation hole 6a to guarantee the connection state of the light outlets 2b, central hole 2a, second ventilation hole 31b, first accommodating cavity 31a and first ventilation hole 3a, guarantee air circulation and improve the sterilization efficiency.

Understandably, when the second ventilation hole 31b is provided on the top of the protruding part 31, since there is a height difference between the top of the protruding part 31 and the germicidal component, the UV light emitted by the germicidal component will not be emitted via the second ventilation hole 31b, so the germicidal device does not need to be provided with a light shield 6. When the second ventilation hole 31b is provided on the lateral side of the periphery of the protruding part 31, ventilation of the germicidal device can be smoother.

In one example of the present invention, the germicidal device also comprises a reflective housing (not marked in the drawing) provided on the inner side of the germicidal component nearby the protruding part, and partial the UV light is emitted via the light outlets after reflection by the reflective housing.

Understandably, the reflective housing is provided between the germicidal component and the protruding part. The reflective housing can reflect UV light emitted to the protruding part to make reflected UV light be emitted via the light outlets to improve the sterilization effect and efficiency.

In one example of the present invention, as shown in FIG. 2, the protruding part and the lamp body are designed into an integrated structure, the periphery of one end of the protruding part 31 connects to the hole wall of the first ventilation hole 3a, and the protruding part 31 and the lamp body 3 are connected by an arc to form a horn shape.

The protruding part 31 and the lamp body 3 are designed into an integrated structure and are connected by an arc to form a horn shape, which enables smoother ventilation of the light, simple structure and low processing cost of lamp body 3. The lamp body 3 made of metal is easy to process and can resist UV light. In this example, the lamp body 3 and the protruding part 31 are made of metal plate.

In one example, the fan component 5 is provided at the joint of the protruding part 31 and the lamp body 3. In another example, the fan component 5 is provided inside the first accommodating cavity 31a. The design of the above position of the fan component 5 can make the overall structure of the germicidal device compact, reduce the product size and shorten the distance between the air inlet and the air outlet of the product.

Figure 8:
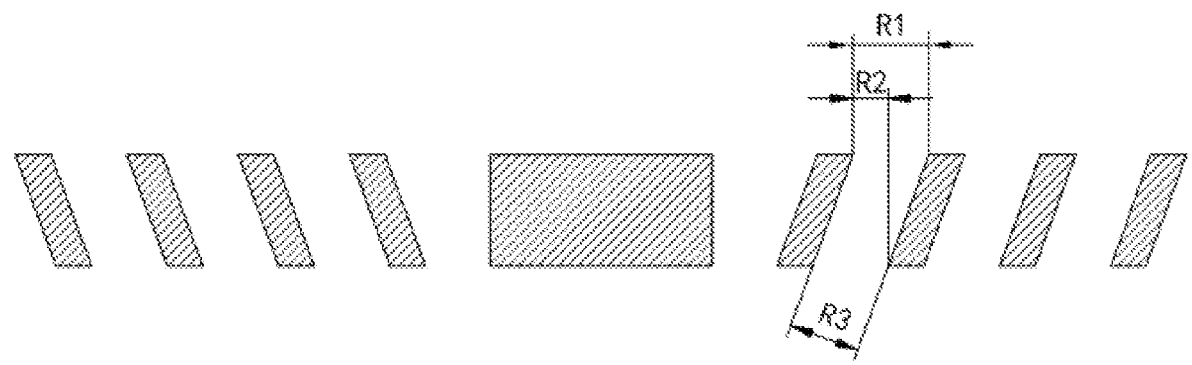
FIG. 8 is the schematic diagram of enlargement of the fourth ventilation hole in FIG. 2.

In one example of the present invention, as shown in FIGS. 1-3, one side of the lamp body 3 departing from the grating component 2 is also provided with a bottom cover 8, the bottom cover 8 is provided with several fourth ventilation holes 8b which connect to the first ventilation hole 3a; As shown in FIG. 8, it is defined as that the width of the fourth ventilation holes 8b is R1 (R1<6.5 mm). In this example, the bottom cover 8 is made of transparent PC. The width of the fourth ventilation holes 8b is limited as less than 6.5 mm, which can prevent fingers from accessing the fan component 5 or other live objects by passing through fourth ventilation holes 8b, guaranteeing the use safety. The width of 6.5 mm is determined according to the characteristics of the product and the dimensions of the test fingers adopted during safety certification of the light. This design can improve the anti-electric shock rate of the product and enables use of non-isolated power supply with a low cost or electronic elements with lower electrical safety performance.

In this example, there is an included angle between the extension direction of the hole wall of the fourth ventilation holes 8b and the first direction, that is, the hole wall of the fourth ventilation holes 8b is inclined corresponding to the air flow direction of the fan component 5. Such design enables that the space between hole walls of the fourth ventilation holes 8b is wide enough to guarantee smooth flowing-out of air and guarantees that when external foreign matters are inserted into the fourth ventilation holes 8b, especially when being parallel to the first direction, such foreign matters will be blocked. Such an alternating-type inclined design solution of fourth ventilation holes 8b achieves both protection effect and air flowing-out efficiency, and is suitable for part injection or demoulding during pressure casting, facilitating processing together with the fan enclosure 51.

As shown in FIG. 8, the fourth ventilation holes 8b are inclined corresponding to the air flowing-in or air flowing-out direction of the fan component 5 (i.e. the first direction). Such inclined design enables the hole space between the two hole wall of the fourth ventilation holes 8b to have a narrow gap R2 in the vertical direction, preventing big foreign matters from being inserted into the fan in the vertical direction; such inclined design also guarantees that the hole space of the fourth ventilation holes 8b has a wide air outlet channel gap R3. Wherein, R3>R2>0 mm.

In this example, as shown in FIG. 2, the position on the bottom cover 8 nearby the fourth ventilation holes 8b is provided with an inclined plane 81, facilitating air flowing-out or flowing-in. The inclined plane 81 can be a conical surface or an arc surface, forming a hole structure whose upper end is narrow and lower end is wide.

In one example of the present invention, as shown in FIG. 2 and FIG. 3, the germicidal device 100 also comprises a lighting component 7 and a second accommodating cavity 8a formed by a bottom cover 8 and lamp body 3 in an enclosing way, and the lighting component 7 is provided inside the second accommodating cavity 8a.

Understandably, the lighting component 7 enables the germicidal device 100 to provide the lighting function.

In one example of the present invention, as shown in FIG. 2 and FIG. 3, the lighting component 7 is provided on one side of the lamp body 3 facing the second accommodating cavity 8a, which enables the fan component 5 to carry out air sterilization and ventilation and disperse heat of the lighting component 7.

The lighting component 7 can be a LED lighting module. In this example, the driving power supply of the LED lighting module is provided on the lamp body 3, which can simplify the structure of the driving power supply and save the cost.

In one example of the present invention, as shown in FIG. 1, FIG. 2, FIG. 3, FIG. 6 and FIG. 7, the lamp cap 1 comprises:
  the first housing part 11 connecting to the grating component 2;
  the second housing part 12, connecting to the first housing part 11 in a dismountable or fixing way for fixing germicidal device 100 in external installation.

Understandably, the second housing part 12 and the first housing part 11 are connected in a dismountable way, which enables better replacement of the lamp cap and facilitates series extension of the germicidal device 100; and also facilitates product assembly, dismounting and repair.

In one example of the present invention, as shown in FIG. 1, FIG. 2 and FIG. 3, when the second housing is provided with a standard screw base structure, it can be directly installed inside traditional lights or on traditional bases for use.

Figure 6:
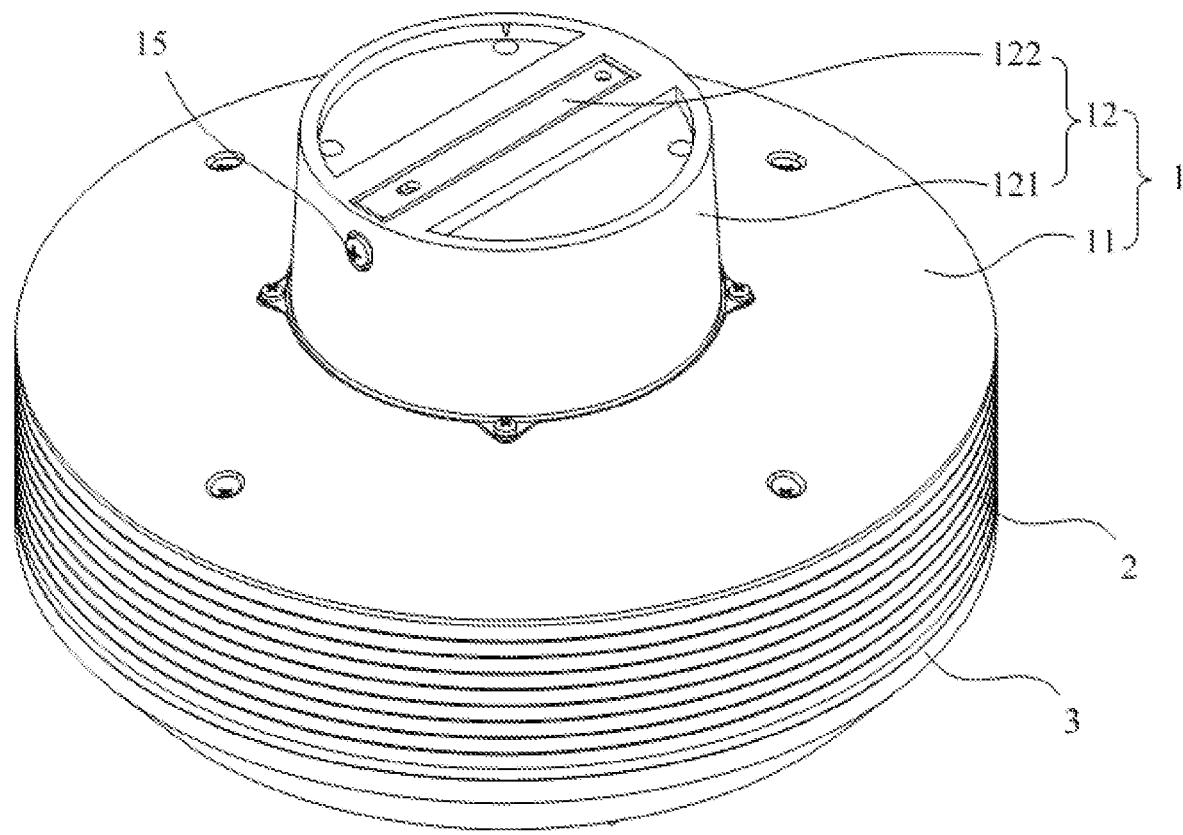
FIG. 6 is a schematic diagram showing the structure of another example of the germicidal device of the present invention.
Figure 7:
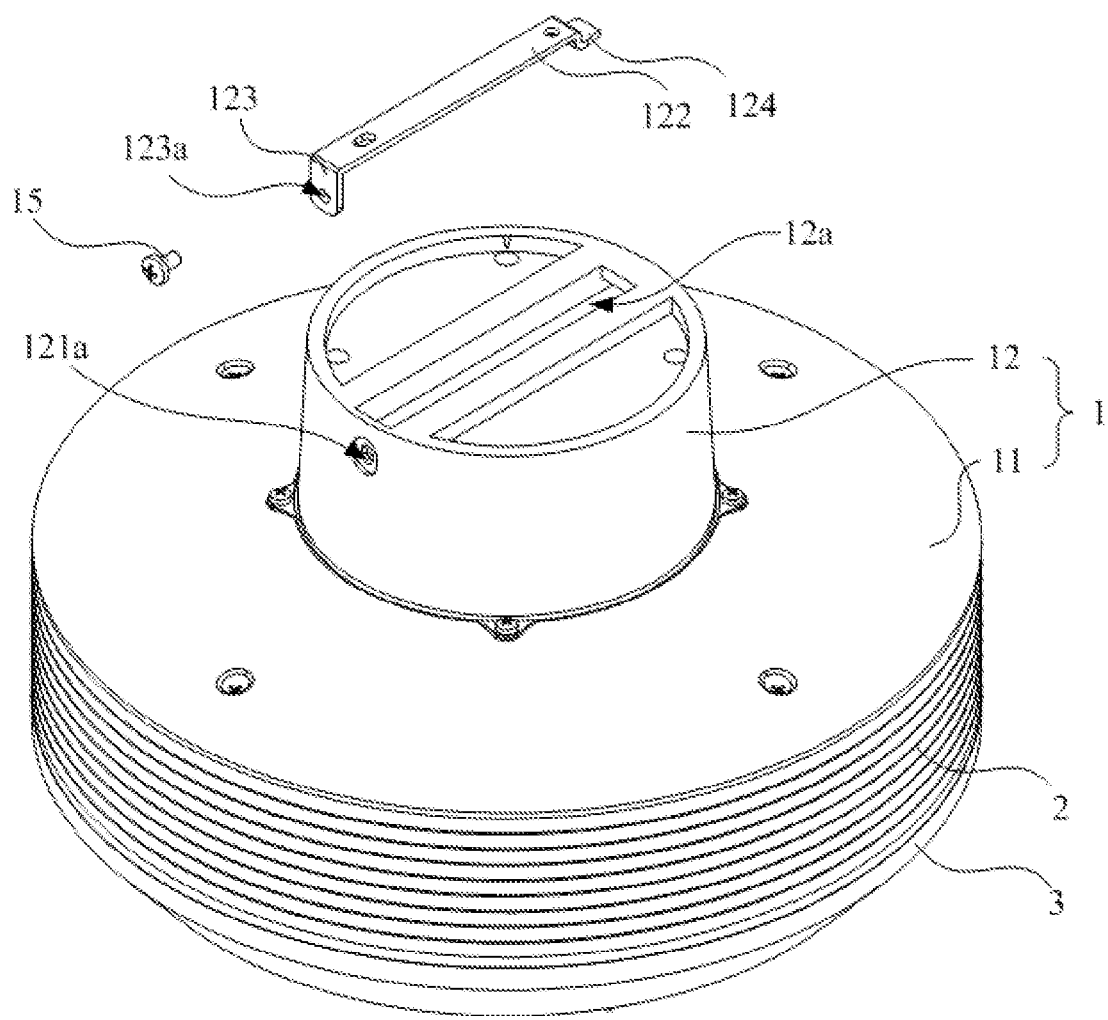
FIG. 7 is the breakdown diagram of the device in FIG. 6.

Or, as shown in FIG. 6 and FIG. 7, in another example of the present invention, the second housing is provided with a fixing seat for fixing in external installation. The second housing part 12 comprises a fixing seat 121 and a mounting board 122, the fixing seat 121 connects to the first housing part 11, one end of the fixing seat 121 departing from the first housing part 11 is provided with a mounting groove 12a, and the mounting board 122 is provided inside the mounting groove 12a in a dismountable way. One end of the mounting board 122 extends in the first direction to form the first mounting part 123; the first mounting part 123 is provided with the first mounting hole 123a; the other end of the mounting board 122 connects to a plug-in part 124 which is in the L shape; the fixing seat 121 is also provided with the first assembly hole 12b and the second assembly hole 12c, both ends of the mounting groove 12a connect to the first assembly hole 12b and the second assembly hole 12c respectively, and the fixing seat 121 is provided with the second mounting hole 121a which connects to the first assembly hole 12b; The second assembly hole 12c is fitted with the plug-in part 124; wherein, the plug-in part 124 is inserted into the second assembly hole 12c, the first mounting part 123 is inserted into the first assembly hole 12b to make the first mounting hole 123a be provided corresponding to the second mounting hole 121a, the fixing seat 121 and the mounting board 122 are connected by the fastener 15 which passes through the first mounting hole 123a and the second mounting hole 121a. In such a way, the product can be installed at a high altitude with only one fastener 15 to reduce the installation difficulty. The fastener 15 can be a bolt or screw, which is not limited here.

It needs to be explained that the mounting board 122 can be installed outside at first, and then the fixing seat 121 of the germicidal device 100 can be installed onto the mounting board 122 to realize installation of the germicidal device 100.

It needs to be explained that the second housing part is provided with the third accommodating cavity 1a in which there is control power supply, and the fan component 5 and the germicidal component 4 electrically connect to the control power supply respectively.

In this example, as shown in FIG. 2, the fan component 5 also comprises a fan enclosure 51 and a fan 52, the fan 52 connects to the lamp body 3 via the fan enclosure 51, or the fan 52 connects to the bottom cover 8 via the fan enclosure 51.

The above description only presents the preferred examples of the invention, and it is not for this reason that the patent scope of the invention is limited. Any equivalent structural transformation made by using the description of the invention and the drawings, or direct/indirect application in other related technical fields under the inventive concept of the invention, is included in the patent protection scope of the invention.

What is claimed is:
1. A germicidal device comprising:
a lamp cap,
a grating component,
a lamp body,
a germicidal component, and
a fan component,
wherein the lamp cap and the lamp body are provided at separate ends of the grating component respectively;
wherein an arrangement direction of the lamp cap, the grating component and the lamp body is in a first direction;
the grating component is provided with a central hole and several baffles, wherein the several baffles are provided at intervals to form several light outlets;
the several light outlets connect to the central hole, the several light outlets extend along the periphery of the grating component, and the light emission direction of the several light outlets is substantially perpendicular to the first direction;
the germicidal component is provided in the central hole for emitting UV light which is emitted via the light outlets;
a bottom of the lamp body is provided with a first ventilation hole which connects to the central hole;
the fan component is provided corresponding to the first ventilation hole for ventilation of the germicidal device; and
wherein the lamp body is for a visible light source.

2. The germicidal device as claimed in claim 1, wherein the germicidal device further comprises a protruding part provided inside the central hole corresponding to the first ventilation hole, and the lamp cap, the lamp body, or the grating component connect to the protruding part; and the germicidal component is provided around the protruding part; and
the protruding part is provided with a second ventilation hole, the first ventilation hole and the central hole connect to the second ventilation hole, respectively.

3. The germicidal device as claimed in claim 2, wherein the germicidal device further comprises a reflective housing, the reflective housing is provided on the inner side of the germicidal component nearby the protruding part, and part of the UV light is emitted via the light outlets after reflection by the reflective housing.

4. The germicidal device as claimed in claim 2, wherein the protruding part is provided with the first accommodating cavity, the first ventilation hole and the second ventilation hole connect to the first accommodating cavity respectively; and
the germicidal device also comprises a light shield provided inside the first accommodating cavity, the light shield is provided with a third ventilation hole, the third ventilation hole and the second ventilation hole are provided at different positions.

5. The germicidal device as claimed in claim 2, wherein the protruding part and the lamp body are formed as an integrated structure, a periphery of one end of the protruding part connects to the hole wall of the first ventilation hole, a protruding part and the lamp body are connected by an arc to form a horn shape, the fan component is provided at a joint between the protruding part and the lamp body;
or, the protruding part is provided with the first accommodating cavity, the first ventilation hole and the second ventilation hole connect to the first accommodating cavity, respectively; the protruding part and the lamp body are formed as an integrated structure, the periphery of one end of the protruding part connects to the hole wall of the first ventilation hole, the protruding part and the lamp body are connected by an arc to form a horn shape, and the fan component is provided inside the first accommodating cavity.

6. The germicidal device as claimed in claim 1, wherein one side of the lamp body departing from the grating component is also provided with a bottom cover, the bottom cover is provided with several fourth ventilation holes, the fourth ventilation holes connect to the first ventilation hole; and a width of the fourth ventilation hole is R1, R1<6.5 mm.

7. The germicidal device as claimed in claim 6, wherein the germicidal device further comprises a lighting component, the bottom cover and the lamp body form the second accommodating cavity in an enclosing way, and the lighting component is located in the second accommodating cavity.

8. The germicidal device as claimed in claim 1, wherein the lamp cap comprises: a first housing part connecting to the grating component; and a dismountable second housing part connecting to the first housing part for fixing the germicidal device to an external installation.

9. The germicidal device as claimed in claim 8, wherein the second housing part comprises a fixing seat and a mounting board, the fixing seat connects to the first housing part, one end of the fixing seat departing from the first housing part is provided with a mounting groove, and the mounting board is provided inside the mounting groove in a dismountable way;

one end of the mounting board extends along the first direction to form the first mounting part; the first mounting part is provided with the first mounting hole; the other end of the mounting board connects to a plug-in part which is in the L shape;

the fixing seat is also provided with the first assembly hole and the second assembly hole, both ends of the mounting groove connect to the first assembly hole and the second assembly hole respectively, and the second assembly hole fits with the plug-in part; the fixing seat is also provided with the second mounting hole which connects to the first assembly hole;

wherein, the plug-in part is inserted into the second assembly hole, the first mounting part is inserted into the first assembly hole to make the first mounting hole and the second mounting hole be provided in a corresponding way, the fixing seat and the mounting board are connected with fasteners which pass through the first mounting hole and the second mounting hole.

10. The germicidal device as claimed in claim 1, wherein the fan component adopts the following ventilation mode: the fan component blows air along the first direction, the light outlets are air inlets, and the first ventilation hole is the air outlet.

* * * * *